US010750968B2

(12) United States Patent
Datta et al.

(10) Patent No.: US 10,750,968 B2
(45) Date of Patent: Aug. 25, 2020

(54) CASCADED BINARY CLASSIFIER FOR IDENTIFYING RHYTHMS IN A SINGLE-LEAD ELECTROCARDIOGRAM (ECG) SIGNAL

(71) Applicant: Tata Consultancy Services Limited, Mumbai (IN)

(72) Inventors: Shreyasi Datta, Kolkata (IN); Chetanya Puri, Kolkata (IN); Ayan Mukherjee, Kolkata (IN); Rohan Banerjee, Kolkata (IN); Anirban Dutta Choudhury, Kolkata (IN); Arijit Ukil, Kolkata (IN); Soma Bandyopadhyay, Kolkata (IN); Arpan Pal, Kolkata (IN); Sundeep Khandelwal, Noida (IN); Rituraj Singh, Kolkata (IN)

(73) Assignee: Tata Consultancy Services Limited, Mumbai (IN)

(*) Notice: Subject to any disclaimer, the term of this patent is extended or adjusted under 35 U.S.C. 154(b) by 257 days.

(21) Appl. No.: 15/883,712

(22) Filed: Jan. 30, 2018

(65) Prior Publication Data

US 2019/0082988 A1 Mar. 21, 2019

(30) Foreign Application Priority Data

Sep. 19, 2017 (IN) .............................. 201721033210

(51) Int. Cl.
*A61B 5/04* (2006.01)
*A61B 5/0452* (2006.01)
(Continued)

(52) U.S. Cl.
CPC .......... *A61B 5/04012* (2013.01); *A61B 5/046* (2013.01); *A61B 5/0452* (2013.01);
(Continued)

(58) Field of Classification Search
CPC . A61B 5/04012; A61B 5/0452; A61B 5/0456; A61B 5/046; A61B 5/0472; A61B 5/7203; A61B 5/7264
See application file for complete search history.

(56) References Cited

U.S. PATENT DOCUMENTS

| 2014/0187989 A1* | 7/2014 | Thakur ................ A61B 5/0452 600/509 |
| 2015/0327781 A1* | 11/2015 | Hernandez-Silveira ..................... A61B 5/7221 600/515 |

FOREIGN PATENT DOCUMENTS

EP 2944251 11/2015

OTHER PUBLICATIONS

Haque, A.K.M.F. et al. (Sep. 2010). "Improved Spectrogram Analysis for ECG Signal in Emergency Medical Applications," *International Journal of Advanced Computer Science and Applications*, vol. 3, No. 3; pp. 39-43.

(Continued)

*Primary Examiner* — Catherine M Voorhees
*Assistant Examiner* — Roland Dinga
(74) *Attorney, Agent, or Firm* — Finnegan, Henderson, Farabow, Garrett & Dunner LLP (57) ABSTRACT

Current technologies analyze electrocardiogram (ECG) signals for a long duration, which is not always a practical scenario. Moreover the current scenarios perform a binary classification between normal and Atrial Fibrillation (AF) only, whereas there are many abnormal rhythms apart from AF. Conventional systems/methods have their own limitations and may tend to misclassify ECG signals, thereby resulting in an unbalanced multi-label classification problem. Embodiments of the present disclosure provide systems and methods that are robust and more efficient for classifying rhythms for example, normal, AF, other abnormal (Continued)

rhythms and noisy ECG recordings by implementing a spectrogram based noise removal that obtains clean ECG signal from an acquired single-lead ECG signal, an optimum feature selection at each layer of classification that selects optimum features from a pool of extracted features, and a multi-layer cascaded binary classifier that identifies rhythms in the clean ECG signal at each layer of the classifier.

9 Claims, 5 Drawing Sheets

(51) Int. Cl.
    *A61B 5/046*     (2006.01)
    *A61B 5/0472*     (2006.01)
    *A61B 5/00*     (2006.01)
    *A61B 5/0456*     (2006.01)

(52) U.S. Cl.
    CPC .......... *A61B 5/0456* (2013.01); *A61B 5/0472* (2013.01); *A61B 5/7203* (2013.01); *A61B 5/7264* (2013.01)

(56) References Cited

OTHER PUBLICATIONS

Langley, P. et al. (2004). "Analysis of RR Interval and Fibrillation Frequency and Amplitude for Predicting Spontaneous Termination of Atrial Fibrillation," *Computers in Cardiology*, vol. 31; pp. 637-640.

Devi, K.L. et al. (Mar. 2015). "Cardiac Biometrics: Human Identity Verification using PCG signals by Binary Decision Tree based SVM," *International Journal of Computational Intelligence and Informatics*, vol. 4, No. 4; pp. 281-286.

Doyle, S. "Cascaded Multi-Class Pairwise Classifier (CASCAMPA) for Normal, Cancerous, and Cancer Confounder Classes in Prostate Histology," *2011 IEEE International Symposium on Biomedical Imaging: From Nano to Macro*, Mar. 30-Apr. 2, 2011, Chicago, IL; pp. 715-718.

Catala, X. (2014-2015). *Design and Implementation of an Atrial Fibrillation Detector Based on Neural Networks* (Master's Thesis). Retrieved from https://riunet.upv.es/bitstream/handle/10251/61694/ TFM.Design%20FA%20detector.xibanez.pdf?sequence=1.

\* cited by examiner

CASCADED BINARY CLASSIFIER FOR IDENTIFYING RHYTHMS IN A SINGLE-LEAD ELECTROCARDIOGRAM (ECG) SIGNAL

PRIORITY CLAIM

This U.S. patent application claims priority under 35 U.S.C. § 119 to: India Application No. 201721033210, filed on Sep. 19, 2017. The entire contents of the aforementioned application are incorporated herein by reference.

TECHNICAL FIELD

The disclosure herein generally relate to electrocardiogram (ECG) signal analysis, and, more particularly, to systems and methods for identifying rhythms in a single-lead electrocardiogram (ECG) signal using a cascaded binary classifier.

BACKGROUND

Atrial Fibrillation (AF) is a common type of heart disease that leads to stroke, heart failure or other complications. Millions of people get affected by AF every year and the prevalence of the disease is likely to increase. Noninvasive detection of AF is a popular area of research for quite a long time. Irregularities in heart beat is considered to be the most common symptom of AF and can be traced in an ECG. However, being an episodic event an accurate detection of AF is not always trivial. Conventional AF detectors have been mostly of atrial activity analysis based or ventricular response analysis-based methods. The absence of P waves or the presence of f waves in the TQ interval are searched in atrial activity analysis-based AF detectors. On the other hand, time, frequency and morphological features are extracted from RR intervals to identity the heart beat irregularity in ventricular response analysis based methods. However, the traditional methods have certain limitations regarding real time deployments, firstly, most of them are validated on clinically accepted multiples of lead ECG signals, recorded for a relatively longer duration. Secondly, algorithms are mostly applied on carefully selected clean data. However, in practical scenario, ECG signals are often noisy in nature. Thirdly, size of the test dataset may often not be adequate for making a conclusion (or decision) thereby result in misclassification. Lastly, most traditional or conventional methods perform binary classification between AF and normal recordings only. However, there are many non-AF abnormal rhythms (e.g., tachycardia, bradycardia, arrhythmia etc.,) which exhibit heart beat pattern similar to AF, however these non-AF abnormal rhythms are not considered for classification. Even if considered them in the dataset makes the classification task more challenging.

SUMMARY

Embodiments of the present disclosure present technological improvements as solutions to one or more of the above-mentioned technical problems recognized by the inventors in conventional systems. For example, in one aspect, a processor implemented method for identifying rhythms in a single-lead electrocardiogram (ECG) signal using a cascaded binary classifier is provided. The method comprising: acquiring, via one or more hardware processors, a single-lead electrocardiogram (ECG) signal that is recorded for a predefined time interval; applying in real-time, via the one or more hardware processors, a spectrogram based noisy data removal technique on the acquired single-lead ECG signal to obtain a clean ECG signal; extracting one or more features from the clean ECG signal; selecting, using an optimum feature selection technique, one or more optimum features from the one or more extracted features, wherein the optimum feature selection technique is at least one of a minimum redundancy maximum relevancy (mRMR) technique and a Maximal Information Coefficient (MIC) technique; and identifying based on the selected one or more optimum features, using a binary cascade classifier, at least one of one or more normal rhythms, a first set of abnormal rhythms, and a second set of abnormal rhythms in at least one of the single-lead electrocardiogram (ECG) signal, and the clean ECG signal.

In an embodiment, the step of applying in real-time, via the one or more hardware processors, a spectrogram based noisy data removal technique on the acquired single-lead ECG signal may comprise: dividing in real-time, the acquired single-lead ECG signal into a plurality of windows; computing in real-time, a spectrogram of each of the plurality of windows; performing in real-time, a comparison of the computed spectrogram of each of the plurality of windows with a dynamically computed threshold, wherein the dynamically computed threshold is based on a signal to noise ratio (SNR); determining in real-time, noise in at least a subset of the plurality of windows based on the comparison; and extracting the clean ECG signal based on the determined noise in the at least a subset of the plurality of windows.

In an embodiment, the noise is determined in the at least a subset of the plurality of windows when each window from the subset have power that is greater than a threshold power.

In another aspect, a system for identifying rhythms in a single-lead electrocardiogram (ECG) signal using a cascaded binary classifier is provided. The system comprising: a memory storing instructions; one or more communication interfaces; and one or more hardware processors coupled to the memory via the one or more communication interfaces, wherein the one or more hardware processors are configured by the instructions to: acquire a single-lead electrocardiogram (ECG) signal that is recorded for a predefined time interval; apply in real-time, a spectrogram based noisy data removal technique on the acquired single-lead ECG signal to obtain a clean ECG signal; extract one or more features from the clean ECG signal; select, using an optimum feature selection technique, one or more optimum features from the one or more extracted features, wherein the optimum feature selection technique is at least one of a minimum redundancy maximum relevancy (mRMR) technique and a Maximal Information Coefficient (MIC) technique; and identify based on the selected one or more optimum features, using a binary cascade classifier, at least one of one or more normal rhythms, a first set of abnormal rhythms, and a second set of abnormal rhythms in at least one of the single-lead electrocardiogram (ECG) signal, and the clean ECG signal.

In an embodiment, the clean ECG signal is extracted by applying in real-time, the spectrogram based noisy data removal technique on the acquired single-lead ECG signal by: dividing in real-time, the acquired single-lead ECG signal into a plurality of windows; computing in real-time, a spectrogram of each of the plurality of windows; performing in real-time, a comparison of the computed spectrogram of each of the plurality of windows with a dynamically computed threshold, wherein the dynamically computed threshold is based on a signal to noise ratio (SNR); determining in real-time, noise in at least a subset of the plurality of windows based on the comparison; and extracting in real-time, the clean ECG signal based on the determined noise in the at least a subset of the plurality of windows.

In an embodiment, noise is determined in the at least a subset of the plurality of windows when each window from the subset have power that is greater than a threshold power.

In yet another aspect, one or more non-transitory machine readable information storage mediums comprising one or more instructions is provided. The one or more instructions which when executed by one or more hardware processors causes acquiring, via the one or more hardware processors, a single-lead electrocardiogram (ECG) signal that is recorded for a predefined time interval; applying in real-time, via the one or more hardware processors, a spectrogram based noisy data removal technique on the acquired single-lead ECG signal to obtain a clean ECG signal; extracting one or more features from the clean ECG signal; selecting, using an optimum feature selection technique, one or more optimum features from the one or more extracted features, wherein the optimum feature selection technique is at least one of a minimum redundancy maximum relevancy (mRMR) technique and a Maximal Information Coefficient (MIC) technique; and identifying based on the selected one or more optimum features, using a binary cascade classifier, at least one of one or more normal rhythms, a first set of abnormal rhythms, and a second set of abnormal rhythms in at least one of the single-lead electrocardiogram (ECG) signal, and the clean ECG signal.

In an embodiment, the step of applying, via the one or more hardware processors, a spectrogram based noisy data removal technique on the acquired single-lead ECG signal may comprise: dividing the acquired single-lead ECG signal into a plurality of windows; computing a spectrogram of each of the plurality of windows; performing a comparison of the computed spectrogram of each of the plurality of windows with a dynamically computed threshold, wherein the dynamically computed threshold is based on a signal to noise ratio (SNR); determining noise in at least a subset of the plurality of windows based on the comparison; and extracting the clean ECG signal based on the determined noise in the at least a subset of the plurality of windows.

In an embodiment, the noise is determined in the at least a subset of the plurality of windows when each window from the subset have power that is greater than a threshold power.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this disclosure, illustrate exemplary embodiments and, together with the description, serve to explain the disclosed principles.

DETAILED DESCRIPTION

Exemplary embodiments are described with reference to the accompanying drawings. In the figures, the left-most digit(s) of a reference number identifies the figure in which the reference number first appears. Wherever convenient, the same reference numbers are used throughout the drawings to refer to the same or like parts. While examples and features of disclosed principles are described herein, modifications, adaptations, and other implementations are possible without departing from the spirit and scope of the disclosed embodiments. It is intended that the following detailed description be considered as exemplary only, with the true scope and spirit being indicated by the following claims.

As mentioned above (in the background section), traditional (or conventional systems and/or methods) have their own limitations and hence may tend to misclassify ECG signals thereby resulting in an unbalanced multi-label classification problem. Embodiments of the present disclosure provide systems and methods for a robust and more efficient technique for classifying normal, AF, other abnormal rhythms and noisy ECG recordings. More particularly, embodiments of the present disclosure provide systems and methods for identifying rhythms in a single-lead electrocardiogram (ECG) signal using a cascaded binary classifier. Embodiments of the present disclosure provide experiment results of a diverse ECG dataset (provided in Physionet challenge 2017) that was used for internal performance evaluation and creating the training models. Information regarding individual recordings were not available regarding the other rhythms in the dataset as all non AF related abnormal rhythms are clubbed together to form a single class. The embodiments of the present disclosure identify rhythms in a single-lead electrocardiogram (ECG) signal by implementing 1) a multi-layer cascaded binary classifier instead of a single multi-class classifier, 2) front end noise removal and 3) optimum feature selection at each layer of classification from a pool of features.

Referring now to the drawings, and more particularly to FIGS. 1 through 5, where similar reference characters denote corresponding features consistently throughout the figures, there are shown preferred embodiments and these embodiments are described in the context of the following exemplary system and/or method.

Figure 1:
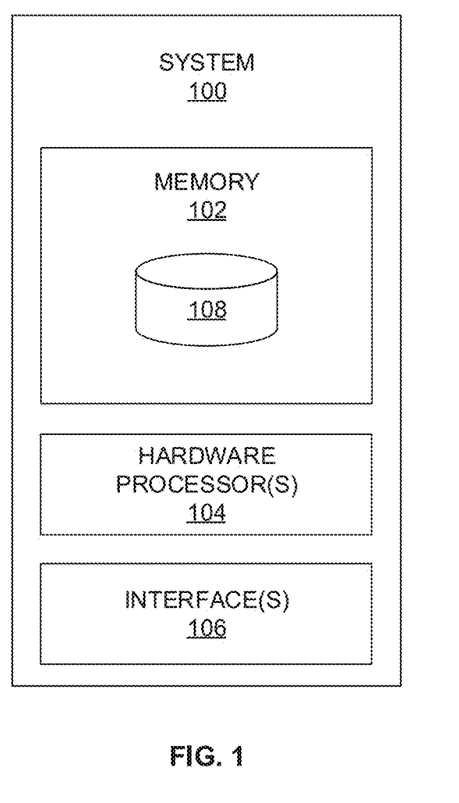
FIG. 1 illustrates an exemplary block diagram of a system for identifying rhythms in a single-lead electrocardiogram (ECG) signal using a cascaded binary classifier in accordance with an embodiment of the present disclosure.

FIG. 1 illustrates an exemplary block diagram of a system 100 for identifying rhythms in a single-lead electrocardiogram (ECG) signal using a cascaded binary classifier in accordance with an embodiment of the present disclosure. In an embodiment, the system 100 includes one or more processors 104, communication interface device(s) or input/output (I/O) interface(s) 106, and one or more data storage devices or memory 102 operatively coupled to the one or more processors 104. The one or more processors 104 may be one or more software processing modules and/or hardware processors. In an embodiment, the hardware processors can be implemented as one or more microprocessors, microcomputers, microcontrollers, digital signal processors, central processing units, state machines, logic circuitries, and/or any devices that manipulate signals based on operational instructions. Among other capabilities, the processor(s) is configured to fetch and execute computer-readable instructions stored in the memory. In an embodiment, the device 100 can be implemented in a variety of computing systems, such as laptop computers, notebooks, hand-held devices, workstations, mainframe computers, servers, a network cloud and the like.

The I/O interface device(s) 106 can include a variety of software and hardware interfaces, for example, a web interface, a graphical user interface, and the like and can facilitate multiple communications within a wide variety of networks N/W and protocol types, including wired networks, for example, LAN, cable, etc., and wireless networks, such as WLAN, cellular, or satellite. In an embodiment, the I/O interface device(s) can include one or more ports for connecting a number of devices to one another or to another server.

The memory 102 may include any computer-readable medium known in the art including, for example, volatile memory, such as static random access memory (SRAM) and dynamic random access memory (DRAM), and/or non-volatile memory, such as read only memory (ROM), erasable programmable ROM, flash memories, hard disks, optical disks, and magnetic tapes. In an embodiment a database 108 can be stored in the memory 102, wherein the database 108 may comprise, but are not limited to information pertaining to signal(s) (e.g., raw data and clean signal), extracted features, optimum features, rhythm types (e.g., normal, abnormal, atrial fibrillation (AF), non-AF, training dataset, test dataset, and the like). In an embodiment, the memory 102 may store the classifiers (e.g., cascaded binary classifier(s)), one or more techniques, for example, spectrogram based noisy data removal technique, feature extraction technique, optimum feature selection technique(s) such as minimum redundancy maximum relevancy (mRMR) technique, and/or maximal Information Coefficient (MIC) technique and the like, which are executed by the one or more hardware processors 104 (or by the system 100) to perform the methodology described herein.

Figure 2:
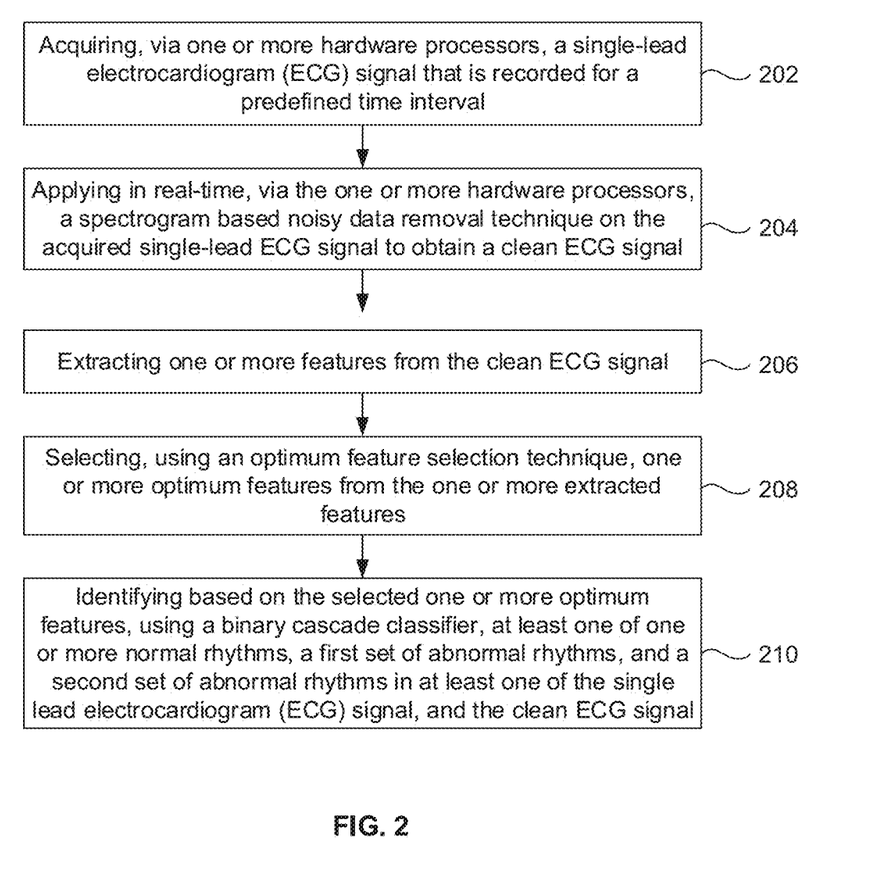
FIG. 2 illustrates an exemplary flow diagram of a method for identifying rhythms in the single-lead electrocardiogram (ECG) signal using the cascaded binary classifier executed by the system of FIG. 1 in accordance with an embodiment of the present disclosure.
Figure 3:
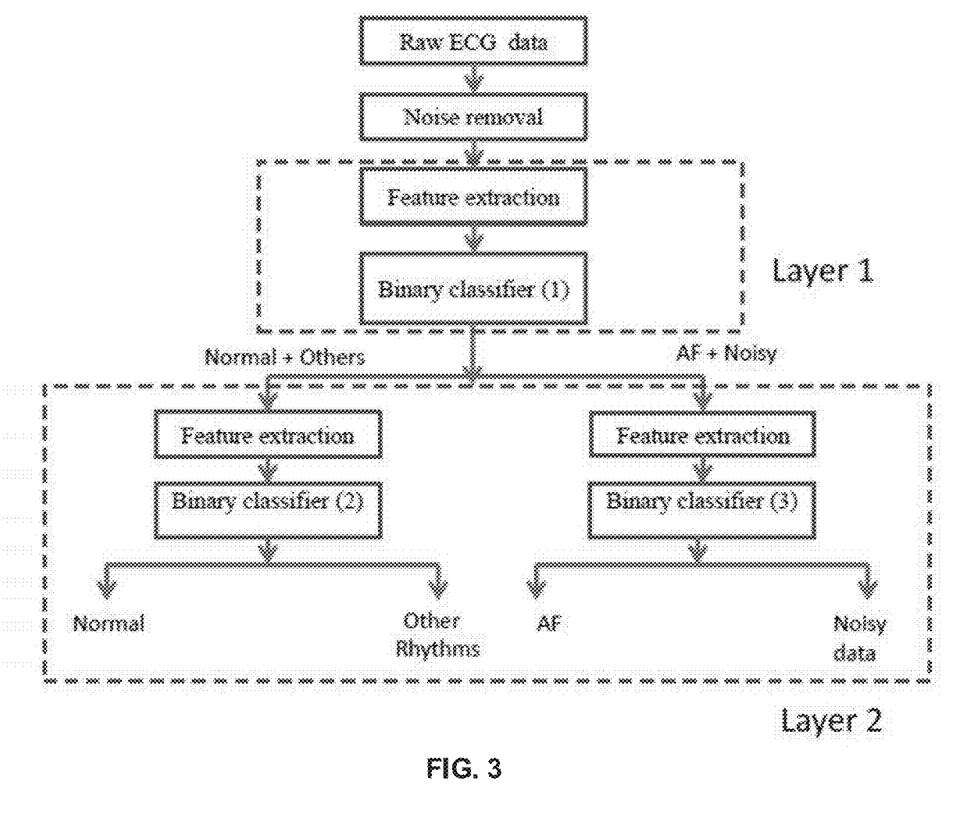
FIG. 3 illustrates an exemplary architecture of the system of FIG. 1 in accordance with an example embodiment of the present disclosure.
Figure 4:
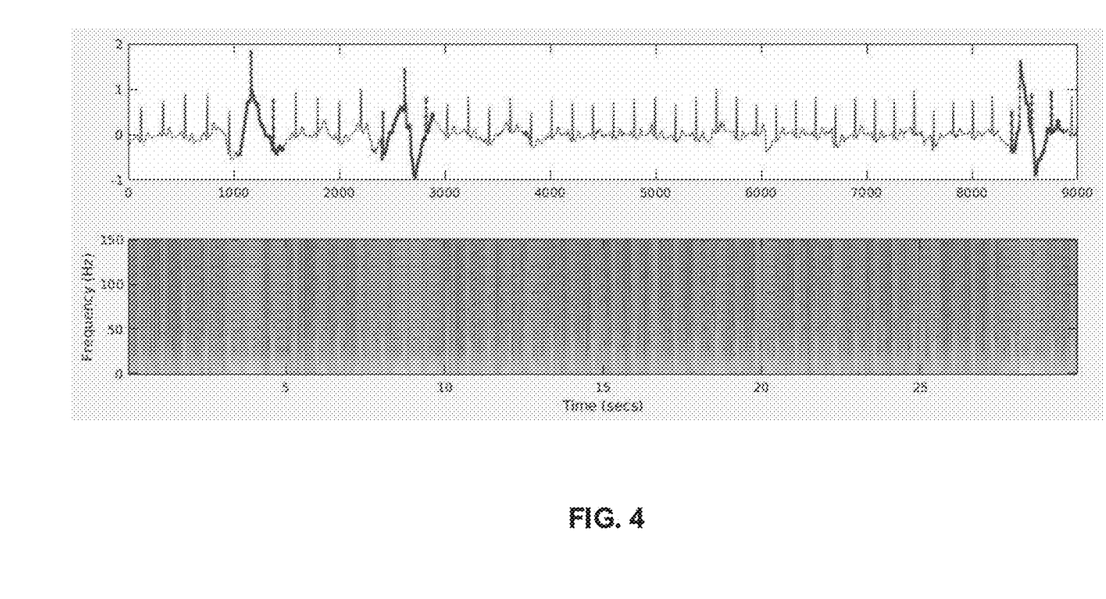
FIG. 4 illustrates a graphical representation of a spectrogram based noise removal in accordance with an example embodiment of the present disclosure.

FIG. 2, with reference to FIG. 1, illustrates an exemplary flow diagram of a method for identifying rhythms in the single-lead electrocardiogram (ECG) signal using the cascaded binary classifier executed by the system 100 of FIG. 1 in accordance with an embodiment of the present disclosure. In an embodiment, the system(s) 100 comprises one or more data storage devices or the memory 102 operatively coupled to the one or more hardware processors 104 and is configured to store instructions for execution of steps of the method by the one or more processors 104. The system 100 stores values/information (and/or parameters, features, rhythms, and the like) associated with ECG signal(s). The steps of the method of the present disclosure will now be explained with reference to the components of the system 100 as depicted in FIGS. 1 and 3, and the flow diagram of FIG. 2. In an embodiment of the present disclosure, at step 202, the one or more hardware processors 104 acquire a single-lead electrocardiogram (ECG) signal (also referred hereinafter ECG signal or ECG waveform) that is recorded for a predefined time interval (e.g., a short duration—say 30 seconds). In an embodiment, the ECG signal may be recorded by using one or more wearable devices (for example, a smart watch, a health band, a fit band, and the like) or any other device that is capable of recording user's health data.

ECG signals, recorded using single-lead, non-medical grade equipment(s) are inherently noisy in nature. Body movement of the user during recording, voltage fluctuation of the sensor device or improper contact between subject body and the sensor electrodes can heavily corrupt the signals. A low frequency component is also present due breathing. Locating and discarding the noisy portions inside a signal is considered a prerequisite before feature extraction and classification. In an embodiment of the present disclosure, at step 204, the one or more hardware processors 104 apply in real-time, a spectrogram based noisy data removal technique on the acquired single-lead ECG signal to obtain a clean ECG signal. In an embodiment of the present disclosure, the clean ECG signal is obtained by dividing the acquired single-lead ECG signal into a plurality of windows, computing a spectrogram of each of the plurality of windows, performing a comparison of the computed spectrogram of each of the plurality of windows with a dynamically computed threshold, wherein the threshold is dynamically computed, determining noise in at least a subset of the plurality of windows based on the comparison, and extracting the clean ECG signal based on the determined noise in the at least a subset of the plurality of windows. In an example embodiment, the steps of dividing, computing a spectrogram, performing a comparison, determining the noise are performed in real-time (or near real-time). In an embodiment, the threshold that is dynamically computed (or computed in real-time) is based on a signal to noise ratio (SNR). In an embodiment of the present disclosure, SNR is measured for all the windows in a recording (or an ECG signal). If the difference between maximum and minimum SNR values is 'n' times (e.g., say 3 times) the minimum value, x % of the maximum SNR is measured as threshold (e.g., say 75% of the maximum SNR is measured as threshold—which is also referred as dynamically computed threshold) for discarding the noisy windows. In other words, 75% of the maximum SNR may be referred as dynamically computed threshold. In an embodiment of the present disclosure, noise is determined in the at least a subset of the plurality of windows when each window from the subset have power (e.g., high spectral power) that is greater than a threshold power above 'X' Hertz (e.g., 50 Hz). In other words, each window from the subset comprising portion of the ECG signal (e.g., the acquired single-lead ECG signal) having power that exceeds the threshold power (also referred as threshold '$P_x$') above 50 Hz are considered as noisy windows and thus discarded to obtain the clean ECG signal.

Important cardiac information, are typically stored within 20 Hz in ECG waveform/signal. Thus, following the spectrogram plot across time axis, if regions between successive RR intervals—wherein R is a point corresponding to the peak of the QRS complex (described below) of the ECG signal; and RR is the interval between successive R's, having high spectral power above 50 Hz (as shown in graphical representation of FIG. 4) are located, that can be safely marked as noisy and are discarded before further processing. More particularly, FIG. 4, with reference to FIGS. 1 through 3, illustrates a graphical representation of a spectrogram based noise removal in accordance with an example embodiment of the present disclosure. Further, the clean signal is passed through a high pass filter (cut-off frequency 0.5 Hz) to remove the baseline movement of the signal. If more than X % (e.g., say 80%) of a certain waveform (e.g., the single-lead ECG signal) is discarded in this process, it is marked as noisy.

Figure 5:
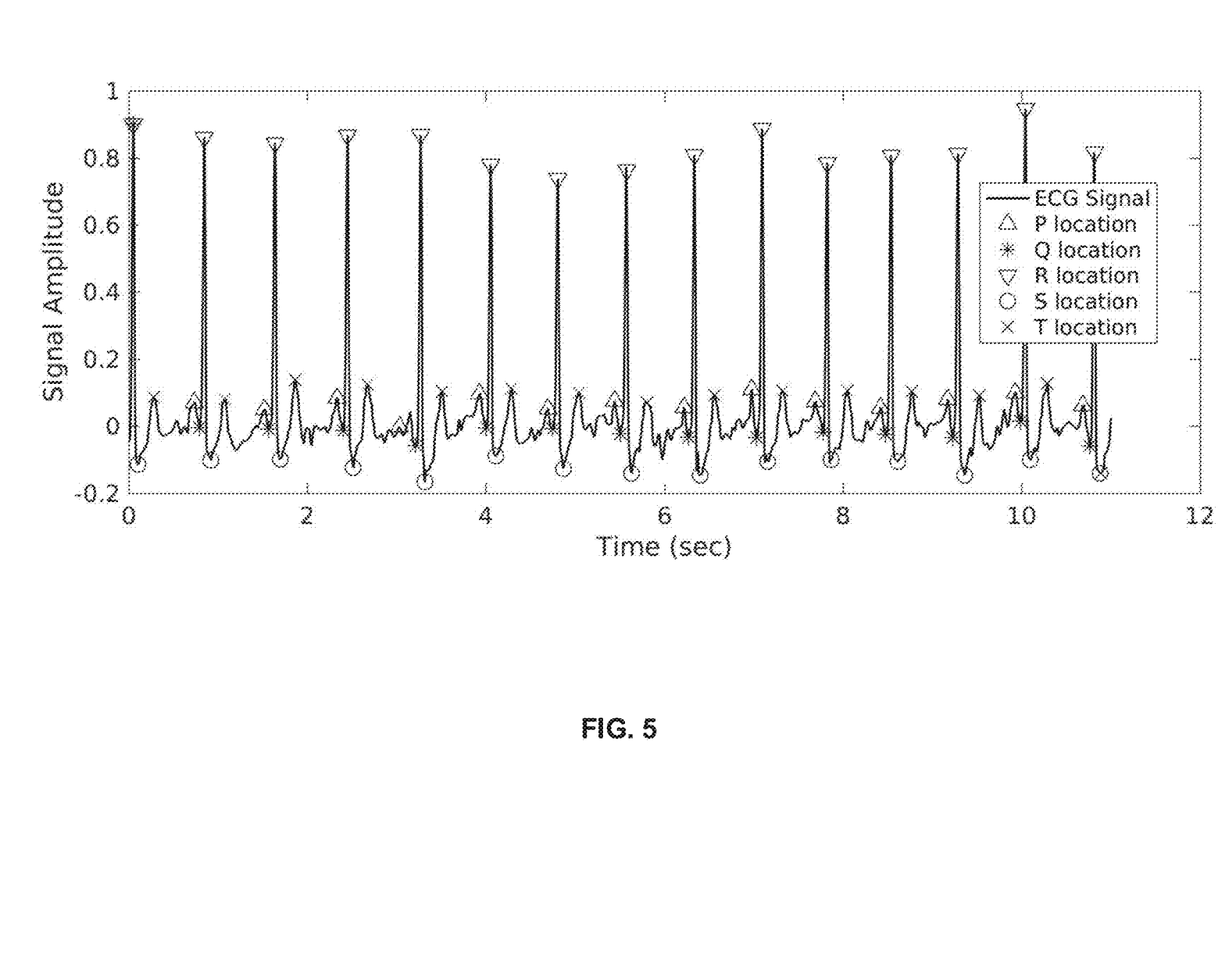
FIG. 5 illustrates a graphical representation of PQRST detection on the single-lead ECG signal in accordance with an example embodiment of the present disclosure.

Identifying the differentiating feature set is considered the most important task of any classification problem. An accurate detection P, Q, R, S, T points are the primary requirement for an accurate feature extraction. The system 100 implements one or more techniques (e.g., a modified Pan-Tompkins technique) to identify QRS complex and R peaks. The QRS complex is a name for the combination of three of the graphical deflections seen on a typical electrocardiogram (EKG or ECG). It is usually the central and most visually obvious part of the tracing. It corresponds to the depolarization of the right and left ventricles of the human heart. In the subsequent stage, P, Q, S and T points are located, taking R peaks as reference points (as shown in FIG. 5). More particularly, FIG. 5, with reference to FIGS. 1 through 4, illustrates a graphical representation of PQRST detection on the single-lead ECG signal in accordance with an example embodiment of the present disclosure. In an embodiment of the present disclosure, at step 206, the one or more hardware processors 104 extract one or more features from the clean ECG signal. The one or more features from the clean ECG signal can be broadly classified into one or more categories illustrated by way of example below:

Morphological ECG Features:

The Morphological ECG features are derived from the PQRST points detected in an ECG waveform as depicted in FIG. 5. In an embodiment of the present disclosure, these features may comprise, but are not limited to, median, range and variance of the corrected QT interval (QTc), QR and QRS widths, slopes of QR, RS and ST intervals, depth of the Q and S points with respect to R, amplitude difference of the TR wave; ratio of the number of P waves to the number of R waves and distance of the ST segment crossing from the S point among others. These features are widely used by clinicians for identifying cardiac abnormalities. It is to be noted that some of these features are indicative of AF while others are for detecting the other abnormal rhythms. For example, in AF, P waves are often absent, hence the ratio of number of P waves to the number of R waves detected is supposed to be very small. Hence, this particular feature was selected by a layer 1 classifier of the cascaded binary classifier and the classifier 3 of layer 2 as depicted in FIG. 3, however, was not selected for the classifier 2 of layer 2. More particularly, FIG. 3, with reference to FIGS. 1-2, illustrates an exemplary architecture of the system 100 of FIG. 1 in accordance with an example embodiment of the present disclosure.

AF Features:

Several features are used to identify AF events. Irregular RR intervals is a very common symptom present in AF patients. There are several metrics to identify the same. Several measurements have been proposed such as for example, AFEvidence, Original Count, Irregularity Evidence, Pace Count, Density Evidence, Anisotropy Evidence, AFEvidence from Lorentz plot of RR intervals. Certain features are derived from the inter beat intervals using Poincare plots also reported commending accuracy in identifying AF. Other features include approximate and sample entropy based features for AF detection as well as coefficient of variation of RR and delta RR intervals.

Heart Rate Variability Features:

Several HRV related features are also incorporated in the proposed analysis. Features for example, pNNx (number of NN intervals above x, normalized by duration of recording, where x lies between 20 and 500 ms), SDNN (standard deviation of NN intervals), SDSD (standard deviation of successive differences) and normalized RMSSD (normalized root mean square of successive differences) were used in identifying cardiovascular diseases. Normalized spectral power of the RR interval time series within the frequency region of 0-0.04 Hz, 0.04-0.15 Hz and 0.15-0.5 Hz are also used.

Frequency Features:

Embodiments of the present disclosure have also explored certain frequency domain features used in biomedical and other applications. Raw time signal is broken into small windows of 'n' seconds duration (e.g., 2 seconds duration) having Y % (e.g., 50%) overlapping using hamming window. Frequency analysis is performed by computing Short Time Fourier Transform (STFT) of each window. Extracted features comprise but are not limited to, mean spectral centroid, spectral roll-off, spectral flux along with normalized spectral power between 0-10 Hz and 10-20 Hz across all windows in a measurement.

Statistical Features:

Statistical features comprise but are not limited to, mean, median, variance, range, kurtosis and skewness of RR intervals and the probability density estimate (PDE) of the RR intervals and the delta RR intervals. Additionally, the number of peaks on the PDE of the RR and delta RR intervals along with the variation of energy in between the RR peaks were also used as features. The Shannon, Tsallis and Renyi entropy, Linear Predictive Coefficients (LPC) of the raw time series data were also used as extracted features by the embodiments of the present disclosure for identifying rhythms in the clean ECG signal.

Features for Other Abnormalities:

Embodiments of the present disclosure (or the system 100) attempt to extract some of the major features to detect arrhythmia or other non-AF related abnormalities present in an ECG signal. In an embodiment of the present disclosure, various features used are extracted using sliding window with 'x' peaks per window (e.g., 6 peaks per window) and its average RR interval, maximum of first difference of number of samples in the window with magnitude exceeding 'z' mV (e.g., where z=0.1 mV), the normalized power spectrum density (nPSD) of the window, etc. The heart rate was estimated using an adaptive frequency tracking algorithm (AMM) to derive the features as mean of RR interval, decrease of HR, max SPI index, average HR, abnormal HR etc.

Features for Detecting Noisy Recordings:

There are several works that detect noise/motion artifacts in the different portions of the signals. However, there are times when the complete signal is not of any use (or very little use) for cardiac abnormality derivation. Embodiments of the present disclosure use domain dependent time and frequency features along with certain statistical features that exploit the rise and fall in the morphology of the ECG signal for improved noise detection. These features discriminate well between the regularities of the clean ECG signal versus the randomness in a noisy waveform.

Referring back to FIG. 2, In an embodiment of the present disclosure, at step 208, the one or more hardware processors 104 select, using an optimum feature selection technique, one or more optimum features from the one or more extracted features.

Feature selection often improves classification accuracy by removing the noisy (irrelevant) features and also reduces the computation time by removing redundant features. A separate feature set is used in each of the three classifiers of the proposed methodology, efficiently chosen using one or more statistical feature selection technique(s) (also referred hereinafter optimum feature selection technique(s)), for example, but are not limited to, a Maximal Information Coefficient (MIC) technique and minimum Redundancy Maximum Relevance (mRMR) technique(s) and are finalized during training phase. Features recommended by medical practitioners for a certain level of classification were also incorporated in the selected feature list.

In an embodiment of the present disclosure, at step 210, the one or more hardware processors 104 identifying based on the selected one or more optimum features, using a binary cascade classifier, at least one of one or more normal rhythms (Normal), a first set of abnormal rhythms (others), and a second set of abnormal rhythms (AF and noisy) in at least one of the single-lead electrocardiogram (ECG) signal, and the clean ECG signal. In an embodiment of the present disclosure, a first binary classifier of the cascaded binary classifier (as depicted in Layer 1) outputs or identifies 'A' set of rhythms (e.g., Normal and Others), and 'B' set of rhythms (e.g., AF and noisy). In an embodiment of the present disclosure, 'A' set of rhythms may be referred as one or more normal rhythms and other rhythms, and wherein 'B' set of rhythms may be referred as AF rhythms and noisy.

In other words, the system 100 classifies an unknown short single-lead ECG signal into one of the four classes including normal, AF, other noisy rhythms and noisy recordings. The major problem of the task is that there is not a single feature exists that can separate four classes at a single shot (or at a single instance). For example, irregular HRV is a common differentiator between normal and AF. However, other rhythms also have the same properties, which introduces ambiguity in a classifier. Thus the embodiments of the present disclosure and the system 100 comprise a cascaded binary classifier that when executed by the one or more hardware processors 104 identifies 'A' set of rhythms may be referred as one or more normal rhythms and other rhythms, and wherein 'B' set of rhythms may be referred as AF rhythms and noisy in the clean ECG signal.

In an embodiment of the present disclosure, the cascaded binary classifier implemented and executed in the system 100 is a three level classifier, connected in two acceded layer as depicted in FIG. 3. At each layer a binary classification is done. The corresponding discriminative features are selected at each level using one or more statistical feature extraction technique(s) as described above. For example, both AF and noisy rhythms contain high frequency noise components. Whereas normal and AF shows similar frequency feature patterns. Thus features like spectral centroid, spectral roll off spectral flux etc., can very well separate them into two classes "normal+others" and "AF+noisy". Now in the next level the system 100 (or the cascaded binary classifier) performs a more fine classification. For example normal ECG signal has a regular pattern in RR intervals and heart rate value lies within a certain limit. Whereas for other rhythms HRV features are not (or may not be) very stable. These kind of features are selected using the optimum feature selection technique(s) when passed through the three level classifier as depicted in FIG. 3. On the other hand, for AF signals, P wave are often found to be missing, that is not found in noisy recordings, moreover noisy recordings have high frequency spectral components which are not present in AF. These kind of features are selected at the third level of classifier (e.g., classifier 3 as depicted in FIG. 3), for classification. In an embodiment of the present disclosure, for each level of classification, Adaptive Boosting (AdaBoost) is used for classification and the details can be found in the draft paper AdaBoost (adaptive boosting) is used in all levels of classification. Adaboost is an ensemble learning approach, where many weak learners are iteratively added in each round of training and a weighting vector is adjusted to reduce the misclassification rate. This technique is less prone to overfitting, more sensitive to noisy data and outliers and can handle the class label imbalance in the training set. For each of the three classifiers, two parameters of the ensemble classifiers, namely, number of learning cycles and learning rate are optimized using Bayesian optimization function.

Experimental Results:

Experiments were performed on the Physionet dataset. This dataset comprised a total of 8528 recordings with mean duration of 32.5 seconds. All of them were single-lead ECG signals, recorded using AliveCor device and sampled at 300 Hz. The distribution of normal, AF, other rhythms and noisy data is largely imbalanced in the dataset. F1-score for normal ($F_{norm}$), AF ($F_{af}$) and other rhythms ($F_{oth}$) were computed for performance analysis and the final accuracy was reported in terms of an illustrative expression as below:

$$F_T = ((F_{norm} + F_{af} + F_{oth})/3)$$

The embodiments of the present disclosure and the proposed methodology of FIG. 2 was initially applied on the entire training dataset using 5-fold cross validation and the performance of the same is shown in Table 1 by way of example below:

TABLE 1

|  | $F_{norm}$ | $F_{af}$ | $F_{oth}$ | $F_T$ |
| --- | --- | --- | --- | --- |
| Average | 0.9095 | 0.7978 | 0.7719 | 0.8264 |
| Standard | 0.0022 | 0.0062 | 0.0040 | 0.0026 |

It can be observed from the above Table 1 that the performance of the proposed methodology of FIG. 2 is stable enough across the folds in a 5-fold cross validation, owing to the small standard deviation values across different test scenarios. It can also be observed that the methodology yields a very high F1-score (average value 0.9) in classifying (or identifying) normal recordings, whereas the F1-score of detecting other rhythms is close to 0.77. A detailed inspection reveals that a good amount of other rhythms are wrongly classified as normal. The unavailability of actual disease information corresponding to each recording in this particular class makes the classification task more challenging to identify the proper features, thus reducing the classification accuracy. A final training model was created on the entire training dataset and evaluated on a subset of the hidden test dataset at a server. Table 2 depicts performance of proposed methodology on a subset of hidden test dataset by way of illustrative example below:

TABLE 2

|  | $F_{norm}$ | $F_{af}$ | $F_{oth}$ | $F_T$ |
| --- | --- | --- | --- | --- |
| Test dataset | 0.92 | 0.86 | 0.74 | 0.84 |

It can be observed from Table 2 that the performance of detecting (or identifying) AF rhythms has significantly improved on the test dataset, compared to internal cross validation on training set. On the other hand, performance of detecting (or identifying) other rhythms has marginally dropped and detection of normal recordings remains almost the same.

Embodiments of the present disclosure and the system 100 identify one or more rhythms in a (short) single-lead ECG recordings, (e.g., say 30 seconds recorded ECG signal) using a series of multi-layer cascaded binary classifiers (also referred as the cascaded binary classifier). The proposed methodology has been successfully validated on Physionet (2017) dataset as mentioned above.

The written description describes the subject matter herein to enable any person skilled in the art to make and use the embodiments. The scope of the subject matter embodiments is defined by the claims and may include other modifications that occur to those skilled in the art. Such other modifications are intended to be within the scope of the claims if they have similar elements that do not differ from the literal language of the claims or if they include equivalent elements with insubstantial differences from the literal language of the claims.

It is to be understood that the scope of the protection is extended to such a program and in addition to a computer-readable means having a message therein; such computer-readable storage means contain program-code means for implementation of one or more steps of the method, when the program runs on a server or mobile device or any suitable programmable device. The hardware device can be any kind of device which can be programmed including e.g. any kind of computer like a server or a personal computer, or the like, or any combination thereof. The device may also include means which could be e.g. hardware means like e.g. an application-specific integrated circuit (ASIC), a field-programmable gate array (FPGA), or a combination of hardware and software means, e.g. an ASIC and an FPGA, or at least one microprocessor and at least one memory with software modules located therein. Thus, the means can include both hardware means and software means. The method embodiments described herein could be implemented in hardware and software. The device may also include software means. Alternatively, the embodiments may be implemented on different hardware devices, e.g. using a plurality of CPUs.

The embodiments herein can comprise hardware and software elements. The embodiments that are implemented in software include but are not limited to, firmware, resident software, microcode, etc. The functions performed by various modules described herein may be implemented in other modules or combinations of other modules. For the purposes of this description, a computer-usable or computer readable medium can be any apparatus that can comprise, store, communicate, propagate, or transport the program for use by or in connection with the instruction execution system, apparatus, or device.

The illustrated steps are set out to explain the exemplary embodiments shown, and it should be anticipated that ongoing technological development will change the manner in which particular functions are performed. These examples are presented herein for purposes of illustration, and not limitation. Further, the boundaries of the functional building blocks have been arbitrarily defined herein for the convenience of the description. Alternative boundaries can be defined so long as the specified functions and relationships thereof are appropriately performed. Alternatives (including equivalents, extensions, variations, deviations, etc., of those described herein) will be apparent to persons skilled in the relevant art(s) based on the teachings contained herein. Such alternatives fall within the scope and spirit of the disclosed embodiments. Also, the words "comprising," "having," "containing," and "including," and other similar forms are intended to be equivalent in meaning and be open ended in that an item or items following any one of these words is not meant to be an exhaustive listing of such item or items, or meant to be limited to only the listed item or items. It must also be noted that as used herein and in the appended claims, the singular forms "a," "an," and "the" include plural references unless the context clearly dictates otherwise.

Furthermore, one or more computer-readable storage media may be utilized in implementing embodiments consistent with the present disclosure. A computer-readable storage medium refers to any type of physical memory on which information or data readable by a processor may be stored. Thus, a computer-readable storage medium may store instructions for execution by one or more processors, including instructions for causing the processor(s) to perform steps or stages consistent with the embodiments described herein. The term "computer-readable medium" should be understood to include tangible items and exclude carrier waves and transient signals, i.e., be non-transitory. Examples include random access memory (RAM), read-only memory (ROM), volatile memory, nonvolatile memory, hard drives, CD ROMs, DVDs, flash drives, disks, and any other known physical storage media.

It is intended that the disclosure and examples be considered as exemplary only, with a true scope and spirit of disclosed embodiments being indicated by the following claims.

What is claimed is:

1. A processor-implemented method, comprising:
   processor implemented method, comprising:
   acquiring, via one or more hardware processors, a single-lead electrocardiogram (ECG) signal that is recorded for a predefined time interval;
   applying in real-time, via the one or more hardware processors, a spectrogram based noisy data removal technique on the acquired single-lead ECG signal to obtain a clean ECG signal, wherein the step of applying, via the one or more hardware processors, a spectrogram based noisy data removal technique on the acquired single-lead ECG signal comprises:
   dividing the acquired single-lead ECG signal into a plurality of windows;
   computing a spectrogram of each of the plurality of windows;
   performing a comparison of the computed spectrogram of each of the plurality of windows with a dynamically computed threshold;
   determining noise in at least a subset of the plurality of windows based on the comparison; and
   extracting the clean ECG signal based on the determined noise in the at least a subset of the plurality of windows;
   extracting one or more features from the clean ECG signal;
   selecting, using an optimum feature selection technique, one or more optimum features from the one or more extracted features, wherein the optimum feature selection technique is at least one of a minimum redundancy maximum relevancy (mRMR) technique and a Maximal Information Coefficient (MIC) technique; and
   identifying based on the selected one or more optimum features, using a binary cascade classifier, at least one of one or more normal rhythms, a first set of abnormal rhythms, and a second set of abnormal rhythms in at least one of the single-lead electrocardiogram (ECG) signal, and the clean ECG signal.

2. The processor implemented method of claim 1, wherein noise is determined in the at least a subset of the plurality of windows when each window from the subset has power that is greater than a threshold power.

3. The processor implemented method of claim 1, wherein the dynamically computed threshold is based on a signal to noise ratio (SNR).

4. A system comprising:
a memory storing instructions;
one or more communication interfaces; and
one or more hardware processors coupled to the memory via the one or more communication interfaces, wherein the one or more hardware processors are configured by the instructions to:
acquire a single-lead electrocardiogram (ECG) signal that is recorded for a predefined time interval;
apply in real-time, a spectrogram based noisy data removal technique on the acquired single-lead ECG signal to obtain a clean ECG signal, wherein the clean ECG signal is extracted by applying the spectrogram based noisy data removal technique on the acquired single-lead ECG signal by:
dividing the acquired single-lead ECG signal into a plurality of windows;
computing a spectrogram of each of the plurality of windows;
performing a comparison of the computed spectrogram of each of the plurality of windows with a dynamically computed threshold;
determining noise in at least a subset of the plurality of windows based on the comparison; and
extracting the clean ECG signal based on the determined noise in the at least a subset of the plurality of windows;
extract one or more features from the clean ECG signal;
select, using an optimum feature selection technique, one or more optimum features from the one or more extracted features, wherein the optimum feature selection technique is at least one of a minimum redundancy maximum relevancy (mRMR) technique and a Maximal Information Coefficient (MIC) technique; and
identify based on the selected one or more optimum features, using a binary cascade classifier, at least one of one or more normal rhythms, a first set of abnormal rhythms, and a second set of abnormal rhythms in at least one of the single-lead electrocardiogram (ECG) signal, and the clean ECG signal.

5. The system of claim 4, wherein noise is determined in the at least a subset of the plurality of windows when each window from the subset have power that is greater than a threshold power.

6. The system of claim 4, wherein the dynamically computed threshold is based on a signal to noise ratio (SNR).

7. One or more non-transitory machine readable information storage mediums comprising one or more instructions which when executed by one or more hardware processors causes:
acquiring, via the one or more hardware processors, a single-lead electrocardiogram (ECG) signal that is recorded for a predefined time interval;
applying in real-time, via the one or more hardware processors, a spectrogram based noisy data removal technique on the acquired single-lead ECG signal to obtain a clean ECG signal, wherein the step of applying, via the one or more hardware processors, a spectrogram based noisy data removal technique on the acquired single-lead ECG signal comprises:
dividing the acquired single-lead ECG signal into a plurality of windows;
computing a spectrogram of each of the plurality of windows;
performing a comparison of the computed spectrogram of each of the plurality of windows with a dynamically computed threshold;
determining noise in at least a subset of the plurality of windows based on the comparison; and
extracting the clean ECG signal based on the determined noise in the at least a subset of the plurality of windows;
extracting one or more features from the clean ECG signal;
selecting, using an optimum feature selection technique, one or more optimum features from the one or more extracted features, wherein the optimum feature selection technique is at least one of a minimum redundancy maximum relevancy (mRMR) technique and a Maximal Information Coefficient (MIC) technique; and
identifying based on the selected one or more optimum features, using a binary cascade classifier, at least one of one or more normal rhythms, a first set of abnormal rhythms, and a second set of abnormal rhythms in at least one of the single-lead electrocardiogram (ECG) signal, and the clean ECG signal.

8. The one or more non-transitory machine readable information storage mediums of claim 7, wherein noise is determined in the at least a subset of the plurality of windows when each window from the subset has power that is greater than a threshold power.

9. The one or more non-transitory machine readable information storage mediums of claim 7, wherein the dynamically computed threshold is based on a signal to noise ratio (SNR).

* * * * *